United States Patent [19]

Stewart et al.

[11] 4,017,600
[45] Apr. 12, 1977

[54] REACTIVATION OF INTERFERON

[75] Inventors: William Edgar Stewart, Herent; Pierre Marie Hendrik Frans de Somer, Leuven, both of Belgium

[73] Assignee: Stichting REGA V.Z.W., Leuven, Belgium

[22] Filed: Apr. 3, 1975

[21] Appl. No.: 564,726

[30] Foreign Application Priority Data

Apr. 3, 1974  Netherlands ...................... 7404590

[52] U.S. Cl. .............................. 424/85; 260/112 R
[51] Int. Cl.² ........................................ A61K 45/02
[58] Field of Search ...................... 424/85; 260/112

[56] References Cited
UNITED STATES PATENTS 3,415,804  12/1968  Polson et al. ........................ 424/85

Primary Examiner—Lewis Gotts
Assistant Examiner—Cary Owens
Attorney, Agent, or Firm—Birch, Stewart, Kolasch and Birch

[57] ABSTRACT

An aqueous interferon solution wherein the interferon has lost at least part of its initial activity is reactivated by treatment with a combination of (a) an agent for disrupting non-covalent bonds, (b) an agent for reducing disulfide bridges, and (c) an anionic or cationic surface-active agent. A heat-treatment is preferably added. Agent (a) is urea or guanidine-hydrochloride and agent (b) is mercaptoethanol or ethanethiol.

11 Claims, No Drawings

REACTIVATION OF INTERFERON

This invention relates to the reactivation of interferon.

Interferon is the name given to a cellular antivirus material which may be recovered from living cells and from extracellular fluids. Its production in the cells may be stimulated by several agents, including in the first place viruses and further a variety of other agents ranging from bacteria to high-molecular polymers. The interferon may be recovered from the cells or extracellular fluids in different degrees of purity and appears to be capable of protecting animal tissues and cells against viral attack. In general, the anti-virus activity of interferon is non-specific in its power to give protection against other viruses in addition to those which have been used for stimulating the cells although differences in sensitivity to interferon have been observed between different viruses. In most cases, interferon is found to give a better protection to tissues and cells of the kind from which it has been produced than to other tissues and cells.

General surveys of the present knowledge about interferon may be found in the books: "Interferon" by J. Vilcek, SpringerVerlag, Vienna-New York, 1969, and "Selective Inhibitors of Viral Functions" by W.A. Carter (Ed), CRC-Press, Cleveland, 1973, which are incorporated herein by way of reference.

Although much work has been done relating to the physical and chemical characterisation of interferon, it has not yet been possible to determine its chemical structure with certainty. It seems evident that interferon is of proteinic nature but most of the details thereof are uncertain. The determination of this chemical structure has been hampered to a great extent by the fact that there seem to be several molecular species of interferon, such species having different molecular weights and different characteristics and their formation being dependent from several factors such as the nature of the cells used for interferon production (e.g. cells from different animal species such as mouse, rabbit, chicken or man, or cells derived from different tissues of a single animal species), the nature of the agent used for production stimulation (e.g. different viruses), the actual production method and the actual method of recovering interferon from cells or fluids.

Further, the production, purification and clinical evaluation of interferon has been hampered up till now by several factors, the most important thereof being the reputed instability of interferon. Although it has been reported that some types of interferon such as human leukocyte interferon and rabbit interferon, are more or less stable against inactivation, other types of interferon are readily inactivated by several circumstances such as prolonged storage, undesired pH values, elevated temperatures and chemical and mechanical manipulations such as shaking, repeated freezing and thawing cycles, frothing during filtration, and the like. Still other types of interferon, such as human fibroblast interferon, have such instability that their activity levels are not reliable. Further, even the relatively most stable types of interferon appear to become labile as soon as a high degree of purity has been reached. To solve these problems it has been proposed to add extraneous proteins to protect the interferon during its purification but this protein addition has many disadvantages because most types of interferon will resist protection and the object of purification is counteracted thereby.

Thus there is need for a method of reactivating interferon that has lost part or all of its activity as a result of its nature or under influence of one of the aforementioned circumstances. More specifically there is need for a method which permits such partially or totally inactivated interferon to be completely reactivated i.e. rendered to its initial activity.

In a co-pending patent application of the same date, (application Ser. No. 564,723, and now U.S. Pat. No. 3,981,991 ) it has already been stated that an aqueous interferon solution wherein the interferon has lost substantially, none of its activity, may be stabilised by treatment with a combination of three reagents, viz, (a) an agent for disrupting non-covalent bonds, such as urea or quanidine-HCl, (b) an agent for reducing disulfide bridges, such as mercapto-ethanol, and (c) an anionic or cationic surfaceactive agent such as sodium dodecyl-sulfate or dodecylamine. When treated with these three agents, the interferon will substantially maintain its initial activity and will be stable against inactivation under influence of the aforesaid circumstances and manipulations.

Quite surprising, it has now been found that an interferon which has already been lowered in activity or perhaps inactivated, may be partially or completely reactivated by treatment with a combination of the same three reagents. A complete reactivation is possible with certainty if the interferon, after addition of the said three reagents is heated at 90°– 105° C for some minutes and the resulting product in that case has substantially the same or even higher activity than the initial, not yet inactivated interferon. Further, the resulting activity will remain constant, thus giving a product which is stable against inactivating circumstances and manipulations.

The invention provides a method of reactivating interferon, which is characterised by treating an aqueous interferon solution wherein the interferon has lost at least part of its initial activity, with a combination of (a) an agent for disrupting non-covalent bonds, (b) an agent for reducing disulfide-bridges, and (c) an anionic or cationic surface active agent. It is preferred to subject the interferon solution after addition of the three said agents to a heat treatment, such as heating at 90° to 105° C for 0.5 to 10 minutes, in order to reach complete reactivation.

Thanks to this discovery, it becomes possible to obtain higher yields in the production and purification of interferon and moreover, to prepare a stable interferon product which is suitable for clinical evaluation.

The mechanism of reactivation brought about by the invention is not yet quite clear. It is presumed, however, that the interferon molecule comprises a polypeptide chain having covalent and non-covalent bonds and further having one or more disulfide bridges, and that the difference between biologically active interferon and an interferon that has been inactivated by the aforesaid circumstances can only be described with reference to a difference in spacial structure or conformation of the molecule. Thus, there will exist an active conformation and an inactive conformation. (Of course, there can be imagined circumstances wherein the interferon molecule is broken down to some extent but such circumstances are not considered here). When the inactivated interferon is treated with the three reagents of the invention, then the molecule is apparently converted by disruption of non-covalent bonds and reduction of disulfide bridges to another conformation having a "linear random coil" and having free sulfhydryl groups, whereupon the anionic or cationic surface-active agent will bind to the charged groups on the polypeptide chain and protect the liberated sulfhydryl groups against reoxidation accompanied by intramolecular or intermolecular reformation of disulfide bridges. These reactions will proceed already for the major part at ambient temperature but may be accelerated or completed by means of a heat treatment such as heating at 90° to 105° C for some time. The resulting product may be freed from the excess of surface-active agent and from the disrupting and reducing agents by means of dialysis, if desired. When the product is incubated later on with a protein-containing medium, such as a medium comprising living cells, the product will spontaneously develop an active conformation which has substantially the initial activity of the corresponding interferon or, in some cases, even a higher activity. The whole process can be described as an reactivation of the inactivated interferon.

It will be evident of course that the invention is not limited by this theoretical explanation. In stead thereof, the invention embraces all features and materials falling within the scope of the appended claims.

In carrying out the method of the invention, the starting material may be any type of interferon which has lost at least part of its initial activity. Useful starting materials may be interferon that has lost part or all of its activity under the influence of inactivating circumstances or manipulations, and as well as interferon that has been recovered in labile or inactivated state dring its production or purification. It will appear from the following examples that mouse interferon (of different types) as well as human fibroblast interferon in a more or less inactivated state may be used as starting materials and many other types of interferon (with the exception of the types which are stable per se) will also be suitable. In most cases, this interferon is available in the form of an aqueous solution, comprising an amount of interferon corresponding to an initial activity between $10^3$ and $10^8$ interferon units per milligram of protein (or between about $10^1$ and $10^6$ interferon units per millimeter of solution) and this solution may be used as such for the method of the invention.

According to the invention, this totally or partially inactivated interferon is treated with a combination of three reagents, viz. an agent for disrupting non-covalent bonds, an agent for reducing disulfide bridges and an anionic or cationic surface-active agent.

Any suitable agent for disrupting non-covalent bonds may be used in the method of the invention. Typical examples are urea and guanidine-hydrochloride whereby urea is preferred.

The amount of such agent used in the described method should be sufficient to bring about unfolding of the polypeptide chain of the interferon molecule in order to result in a "linear random coil". In general, the amount of urea as used is such that the resulting solution comprises from 0.1 to 10 M of urea and preferably, the concentration is chosen to be 5M of urea. Lower concentrations than 0.1 M will be without effect and higher concentrations than 10 M are useless because the saturation point has been reached then.

Any suitable agent for reducing disulfide bridges may be used in the method of the invention. A typical example is ethanethiol or mercaptoethanol. The amount thereof as used should be sufficient to reduce all disulfide bridges in the interferon molecule as far as they are present therein. In most cases, the amount of mercaptoethanol is such that the resulting solution comprises at least $10^{-2}$M of mercapto-ethanol. Lower amounts than $10^{-2}$M will have little or no effect. An upper limit can hardly be given because higher amounts are not harmful. It is preferred to use concentrations of about $1.4 \times 10^{-2}$M to $1.4 \times 10^{-1}$M of mercaptoethanol in the solution.

Any suitable anionic or cationic surface-active agent may be used in the method of the invention. The anionic agent will usually be an alkyl sulfate having 8 to 22 carbon atoms in its alkyl group, such as sodium dodecylsulfate or sodium decylsulfate, or else a corresponding alkyl sulfonate such as sodium dodecylsulfonate. The cationic agent will be, in general, an alkylamine having 8 to 22 carbon atoms in its alkyl group, such as dodecylamine or decylamine. The amount of this agent as used should be sufficient to bind the protein and to protect the sulfhydryl groups of the interferon molecule liberated by the aforesaid reduction agent. In order to be sure of the desired effect, a 1-fold to 5-fold excess of surface-active agent calculated on the total amount of protein in solution will be used in most cases. If the starting material is an interferon solution comprising about $10^4$ interferon units per millimeter, this will mean that the solution should comprise at least $1 \times 10^{-3}$M and at most $1 \times 10^{-1}$M of surface-active agent. An amount of $3.5 \times 10^{-3}$M to $3.5 \times 10^{-2}$M of sodium dodecylsulfate is preferred in that case.

The addition sequence of the three reagents is not critical although it is preferred to add the surface-active agent simultaneously with or prior to the other two agents in order to be sure that this surface-active agent is able to react with the polypeptide to protect the sulfhydryl groups as soon as they have been liberated by the reduction agent. It is preferred to add all three agents substantially at the same time or one shortly after the other.

Although, in general, the three reagents will already react at ambient temperature with the inactivated interferon, the reaction need not always reach completion then. Thus, if the starting material is an aqueous interferon solution which has been inactivated completely by boiling, a treatment with the three reagents at ambient temperature will only result in a reactivation to reach about 50% of the initial interferon activity. In such cases, it is preferred to subject the interferon solution to a heat treatment after addition of the three reagents. This heat treatment may e.g. comprise heating at a temperature of 90° to 105° C for 0.5 to 10 minutes, and preferably heating the solution at 100° C for 1 minute. Such a heat treatment may result in any case in a complete reactivation of the interferon.

After the reaction with the three reagents, the excess of surface-active agent and the total amount of the other two reagents may be removed by dialysis, if desired. However, this removal is not absolutely necessary for further utilisation of the product.

Thanks to the method of the invention, a substantial to complete reactivation of the inactivated interferon and moreover, a stabilisation of the product against subsequent inactivating circumstances and manipulations can be reached. It appears that inactivated human fibroblast interferon as well as inactivated mouse interferon will resume their initial activity by means of treatment with urea, mercaptoethanol and sodium dodecylsulfate, followed by heat treatment. Moreover, the resulting product appears to be stable against subsequent heating at 56° C and 100° C.

It must be observed that the same effect cannot be obtained with only one or two of the aforesaid three reagents. Thus, urea and mercaptoethanol, when used alone or together, will have no reactivating effect but rather an instability-provoking effect on interferon in spite of the fact that flocculated parts of the interferon are re-dissolved thereby. Sodium dodecylsulfate or a combination of sodium dodecylsulfate and urea may lead to partial reactivation but this reactivation remains very small. Thus, starting with completely inactivated human fibroblast interferon or mouse interferon and using these two reagents, not more than about 5% of the initial activity may be recovered at room temperature and not more than about 10% of the initial activity may be recovered by 1 minute boiling at 100° C. This means that a combination of three reagents together or not together with a heat treatment will always be necessary for reaching complete reactivation.

The method of reactivating interferon as disclosed in this specification offers a possibility for recovering all types of interferon which have lost part of their activity during purification and moreover recovering all interferon compositions which have been reduced in activity during prolonged storage. Thus, better use of any interferon that has already been produced in an earlier stage may be made. The fact that this reactivated interferon is stable against further inactivation makes it possible to use this interferon in a variety of ways and to apply it clinically. A relatively pure reactivated interferon having an activity of about $10^3$ to $10^8$ interferon units per milligram of protein may thus be administered clinically in reactivated form. In general, proteins will bind only 1;44 grams of sodium dodecylsulfate per gram of protein and this means that a dosage comprising millions of units of interferon will only comprise a few micrograms of sodium dodecylsulfate. Thus, there will be no risk for complications during clinical administration.

The following examples are meant for illustration purposes only and not for limitation of the scope of the invention.

EXAMPLE 1

The starting material was a solution of mouse interferon derived from cells of the L-$_{929}$ type stimulated by Newcastle Disease virus (NDV). The solution was acidified to a pH of 2, whereupon extraneous proteins were precipitated by addition of ammonium sulfate until a saturation degree of 20% at 20° C was reached. The clarified solution was adjusted to a pH of 7.2 by dialysis against a 0.01 M TRIS-HCl buffer. The resulting purified solution had an activity of $10^4$ interferon units per milliliter (determined by biological assay).

An aliquot portion of 1 ml of this purified interferon solution was placed in a test tube which was immersed in a beaker filled with boiling water. After 2½ minute heating at 100° C, the interferon was substantially completely inactivated since its activity was reduced to less than $10^1$ interferon units per milliliter.

A number of further aliquot portions of 1 ml of purified interferon solution was first heated at 100° C in the aforesaid way during 2½ minutes. After cooling the inactivated solutions, one or more reagents selected from the group of solid urea, liquid mercapto-ethanol and an aqueous solution of sodium dodecylsulfate (SDS) were added thereto in such amounts that the end concentration of these reagents, as far as present, was 5 M of urea, $1.4 \times 10^{-2}$M of mercapto-ethanol and $3.5 \times 10^{-3}$M of SDS. Water was also added in some cases in order to equalize the dilution factor for all tests. For any reagent or combination of reagents, the reaction was effected one time at room temperature and one time at elevated temperature. To this latter end, the solution was heated for 1 minute at 100° C after addition of the reagents. Thereupon, the activities of the resulting mixtures were evaluated by means of biological assay. The results are specified in the following table 1.

The term "titer" therein is an indication for the decimal logarithm of the activity (in interferon units per milliliter). All titer values are an average of three separate experiments.

TABLE 1

| Inactivation | Reagents for Reactivation | Titer |
| --- | --- | --- |
| None | None | 4.0 |
| 100° C-2½ min. | None | <1.0 |
| ″ | Urea | <1.0 |
| ″ | Urea + 100° C-1 min. | <1.0 |
| ″ | Mercapto-ethanol | <1.0 |
| ″ | Mercapto-ethanol + 100° C-1 min. | <1.0 |
| ″ | Urea + Mercapto-ethanol | <1.0 |
| ″ | Urea + Mercapto-ethanol + 100° C-1 min. | <1.0 |
| ″ | SDS | 2.7 |
| ″ | SDS + 100° C-1 min. | 3.0 |
| ″ | SDS + Urea | 2.0 |
| ″ | SDS + Urea + 100° C-1 min. | 2.5 |
| ″ | SDS + Mercapto-ethanol | 3.7 |
| ″ | SDS + Mercapto-ethanol + 100° C-1 min. | 3.9 |
| ″ | SDS + Urea + Mercapto-ethanol | 3.7 |
| ″ | SDS + Urea + Mercapto-ethanol + 100° C-1 min. | 4.0 |

It follows from the Table 1 that a substantial to complete reactivation of inactivated interferon may be obtained by treatment with a combination of the three reagents according to the invention. Treatment of the inactivated interferon with SDS alone or with a combination of SDS with one of the other reagents will result in certain restoration of activity but even after 1 minute boiling at 100° C, this reactivation is not complete. A treatment with urea and mercapto-ethanol, either alone or in combination, does not bring about any reactivation.

EXAMPLE 2

A number of interferon solutions of various sources and activities were first inactivated and then subjected to a reactivation treatment according to the invention.

The solutions used for this example were:

1. a solution of mouse interferon produced in L-cells inoculated with ultraviolet irradiated Newcastle Disease virus (NDV-UV). This interferon comprised 0:5 % of serum albumin and initially had an activity of $10^8$ interferon units per mg of protein or $10^6$ interferon units per milliliter.

2. a solution of mouse interferon produced in L$_{929}$ cells inoculated with Newcastle Disease virus (NDV). Three types were used, having activities of $10^4$, $10^6$ and more than $10^7$ interferon units per mg of protein, respectively. This corresponds in each case to $10^4$ interferon units per ml.

3. a solution of mouse interferon produced in interferonprimed Lpa cells inoculated with the MM strain of encephalomyocarditis virus. Two types were used, having activities of $10^4$ and $5 \times 10^6$ interferon units per mg of protein, respectively. This corresponds in both cases to $10^4$ interferon units per ml.

4. a solution of human diploid fibroblast interferon produced in human diploid fibroblast cells induced by polyriboinsinic acid and polycytidylic acid (Poly I, poly C) and subsequently "superinduced" according to the method of Havell and Vilcek (Antimicrobial Agents Chemother., 2, 476–484 (1972). Three types were used, having activities of $10^4$, about $10^3$ and about $10^3$ interferon units per ml respectively.

The biological assays to evaluate the interferon activity were effected by determination of the endpoint where 50% plaque reduction occurred. This was done with vesicular stomatitis virus in $L_{929}$ cells for mouse interferon and with the same virus in $L_{132}$ fibroblast cells for human interferon.

The inactivation was effected in various ways viz. by 2½ minutes boiling at 100° C, by 30 minutes heating at 56° C, by 100 times freezing and thawing, or by adding urea and mercaptoethanol in such amounts that their end concentrations were 5 M of urea and $1.4 \times 10^{-2}$M of mercapto-ethanol respectively. These inactivation processes are specified in Table 2. Heating at 100° C appeared to be the most effective way for inactivation. The rate and degree of inactivation were independent of the total amount of extraneous proteins.

After inactivation, the interferon solutions were subjected to a reactivation treatment according to the invention. This treatment comprised an addition of solid urea, liquid mercaptoethanol and an aqueous solution of sodium dodecylsulfate in such amounts that their end concentrations were 5 M of urea, $1.4 \times 10^{-2}$M of mercapto-ethanol and $3.5 \times 10^{-3}$M of sodium dodecyl-sulfate respectively, followed by heating the whole composition at 100° C for one minute.

Further details relating to the starting material, initial titer, means of inactivation, titer after inactivation and the titer after reactivation are presented in the following Table 2. The term "titer" means the decimal logarithm of the activity in terms of interferon units per milliliter. The term "specific activity" means the activity per milligram of protein.

Table 2

| Interferon | Initial Titer | Inactivation Process | Titer after Inactivation | Titer after reactivation |
|---|---|---|---|---|
| Mouse L NDV-UV containing 0.5% serum albumin | 4.0 | 100° C-2½ min. | <1.0 | 4.0 |
| Mouse L-929 NDV Spec.Act. $10^4$ | 4.0 | 100° C-2½ min. | <1.0 | 4.5 |
| Interferon-primed mouse L-paMM Spec.Act. $10^4$ | 4.7 | 100° C-2½ min. | <1.0 | 5.3 |
| Interferon-primed mouse Lpa-MM Spec.Act. $5 \times 10^6$ | 4.3 | 100° C-2½ min. | <1.0 | 4.8 |
| Mouse $L_{929}$-NDV Spec.Act. $>10^7$ | 3.7 | 100° C-2½ min. | <1.0 | 3.8 |
| Mouse $L_{929}$-NDV Spec.Act. $10^6$ | 4.0 | 100° C-2½ min. | <1.0 | 4.0 |
| " | 4.0 | 56° C-30 min. | 3.2 | 4.0 |
| " | 4.0 | Freeze-thaw cycles (100 ×) | 2.9 | 4.0 |
| " | 4.0 | 5M urea + $1.4 \times 10^{-2}$M Mercapto-ethanol | 3.0 | 4.0 |
| Human diploid poly I. poly C superinduced | 4.0 | 100° C-2½ min. | <1.0 | 4.0 |
| " | 2.3 | 100° C-2½ min. | <1.0 | 3.0 |
| " | 3.3 | 100° C-2½ min. | <1.0 | 3.3 |

It follows from Table 2, that a complete reactivation may be obtained with several different starting materials.

What we claim is:

1. A method of reactivating interferon, comprising the following steps:
   a. providing an aqueous interferon solution which has lost at least part of its initial activity; and
   b. treating said interferon solution with a combination of:
      i. urea or guanidine-hydrochloride as an agent for disrupting non-covalent bonds,
      ii. mercaptoethanol or ethanethiol as an agent for reducing disulfide bridges, and
      iii. a surface-active agent selected from the group consisting of sodium dodecylsulfate, sodium decylsulfate, sodium dodecylsulfonate, dodecylamine and decylamine, so as to obtain an aqueous interferon solution which has been reactivated substantially to its initial activity.

2. The method as claimed in claim 1, wherein said agent for disrupting non-covalent bonds is urea.

3. The method as claimed in claim 1, wherein said agent for reducing disulfide bridges is mercaptoethanol.

4. The method as claimed in claim 1, further comprising the step of subjecting said interferon solution to a heat treatment after the addition of said combination of agents thereto.

5. The method as claimed in claim 4, wherein said heat treatment is carried out at 90° to 105° C. for 0.5 to 10 minutes.

6. The method as claimed in claim 1, including the further step of:
   c. removing an excess of surface-active agent and all of said other two agents by means of dialysis.

7. A method of reactivating interferon, comprising the steps of:
   a. providing an aqueous interferon solution having lost at least part of its initial activity and comprising from about $10^1$ to about $10^6$ interferon units per milliliter; and b. treating said interferon solution with a combination of:
  i. urea or guanidine-hydrochloride as an agent for disrupting non-covalent bonds;
  ii. mercaptoethanol or ethanethiol as an agent for reducing disulfide bridges; and
  iii. an agent selected from the group consisting of sodium dodecylsulfate, sodium decylsulfate, sodium dodecylsulfonate, dodecylamine and decylamine as a surface-active agent; said three agents being used in such amounts that the resulting solution comprises from 0.1 to 10 M of urea or guanidine-hydrochloride, at least $10^{-2}$M of mercaptoethanol or ethanethiol, and a onefold to fivefold excess of said surface-active agent calculated on the total amount of proteins in solution, respectively; so as to obtain an aqueous interferon solution which has been reactivated substantially to its initial activity.

8. The method as claimed in claim 7, wherein said interferon solution comprises about $10^4$ interferon units per milliliter and wherein said three agents are used in such amounts that the resulting solution comprises about 5 M of urea, from $1.4 \times 10^{-2}$ to $1.4 \times 10^{-1}$M of mercaptoethanol and from $1 \times 10^{-3}$ to $1 \times 10^{-1}$ M of surface-active agent, respectively.

9. The method as claimed in claim 7, including the further step of:
  c. removing an excess of surface-active agent and all of said other two agents by means of dialysis.

10. The method as claimed in claim 7, further comprising the step of subjecting said interferon solution to a heat treatment afer the addition of said combination of agents thereto.

11. The method as claimed in claim 10, wherein said heat treatment is carried out at 90° to 105° C. for 0.5 to 10 minutes.

* * * * *